(12) United States Patent
Møller (10) Patent No.: US 8,864,721 B2
(45) Date of Patent: Oct. 21, 2014

(54) GEARING MECHANISM FOR A DOSE DELIVERY DEVICE

(75) Inventor: Claus Schmidt Møller, Fredensborg (DK)

(73) Assignee: Eli Lilly and Company, Indianapolis, IN (US)

( * ) Notice: Subject to any disclaimer, the term of this patent is extended or adjusted under 35 U.S.C. 154(b) by 54 days.

(21) Appl. No.: 13/825,396

(22) PCT Filed: Sep. 23, 2011

(86) PCT No.: PCT/DK2011/000103
§ 371 (c)(1),
(2), (4) Date: Mar. 21, 2013

(87) PCT Pub. No.: WO2012/037938
PCT Pub. Date: Mar. 29, 2012

(65) Prior Publication Data
US 2013/0184653 A1 Jul. 18, 2013

(30) Foreign Application Priority Data
Sep. 24, 2010 (DK) .................................. 2010 00872

(51) Int. Cl.
*A61M 5/00* (2006.01)
*A61M 5/315* (2006.01)
(52) U.S. Cl.
CPC ....... *A61M 5/31528* (2013.01); *A61M 5/31525* (2013.01); *A61M 5/31558* (2013.01)
USPC .......................................... 604/211; 604/189

(58) Field of Classification Search
USPC ........................... 604/189, 207–211, 218–231
See application file for complete search history.

(56) References Cited

U.S. PATENT DOCUMENTS

| 5,114,406 | A | 5/1992 | Gabriel et al. |
| 5,279,585 | A | 1/1994 | Balkwill |
| 5,391,157 | A | 2/1995 | Harris et al. |
| 5,688,251 | A | 11/1997 | Chanoch |
| 5,725,508 | A | 3/1998 | Chanoch et al. |
| 5,743,889 | A | 4/1998 | Sams |
| 5,957,896 | A | 9/1999 | Bendek et al. |
| 6,221,046 | B1 | 4/2001 | Burroughs et al. |
| 6,221,053 | B1 | 4/2001 | Walters et al. |

(Continued)

FOREIGN PATENT DOCUMENTS

| EP | 0327910 | 8/1989 |
| EP | 1568389 | 8/2005 |

(Continued)

*Primary Examiner* — Kevin C Sirmons
*Assistant Examiner* — Phillip Gray
(74) *Attorney, Agent, or Firm* — Edward J. Prein (57) ABSTRACT

The invention relates to a gearing mechanism for a dose delivery device wherein the dose can be set by rotating a dose setting member (2, 102), and by which the dose setting member (2, 102) and a push-button (4) elevates from one end of the device proportional to the set dose from a position fixed relative to a housing (1, 101), and by which an injection of the set dose can be done by pressing the push-button back to its not elevated position, moving a piston rod (10, 110) cooperating with the piston in an cartridge (12, 112) and expelling a medicament out of the through a needle. The gearing mechanism is arranged in the device in such a way, that the loss of energy is very low.

8 Claims, 7 Drawing Sheets

(56) References Cited

U.S. PATENT DOCUMENTS

| | | |
|---|---|---|
| 6,235,004 B1 | 5/2001 | Steenfeldt-Jensen et al. |
| 6,945,961 B2 | 9/2005 | Miller et al. |
| 7,094,221 B2 | 8/2006 | Veasey et al. |
| 7,361,161 B2 | 4/2008 | Bainton |
| 7,427,275 B2 | 9/2008 | DeRuntz et al. |
| 7,553,299 B2 | 6/2009 | Veasey et al. |
| 7,678,085 B2 | 3/2010 | Graf |
| 7,704,238 B2 | 4/2010 | Diller et al. |
| 7,771,400 B2 | 8/2010 | Nielsen |
| 7,850,662 B2 | 12/2010 | Veasey et al. |
| 7,905,867 B2 | 3/2011 | Veasey et al. |
| 7,918,833 B2 | 4/2011 | Veasey et al. |
| 2005/0033244 A1 | 2/2005 | Veasey et al. |
| 2006/0258988 A1 | 11/2006 | Keitel et al. |
| 2007/0093761 A1 | 4/2007 | Veasey et al. |
| 2009/0012479 A1 | 1/2009 | Moller et al. |
| 2009/0254047 A1 | 10/2009 | Thorgersen et al. |
| 2009/0264828 A1 | 10/2009 | Dette et al. |
| 2009/0275916 A1 | 11/2009 | Harms et al. |
| 2009/0287162 A1 | 11/2009 | Veasey et al. |
| 2010/0094253 A1 | 4/2010 | Boyd et al. |
| 2011/0319835 A1 | 12/2011 | Burren et al. |
| 2013/0150799 A1 | 6/2013 | Radmer et al. |

FOREIGN PATENT DOCUMENTS

| | | |
|---|---|---|
| EP | 2047878 | 2/2011 |
| WO | 2009039851 | 4/2009 |
| WO | 2010072229 | 7/2010 |
| WO | WO 2010072229 A1 * | 7/2010 |

* cited by examiner

GEARING MECHANISM FOR A DOSE DELIVERY DEVICE

FIELD OF INVENTION

The invention relates to a dose delivery device, wherein a dose can be set by rotating a dose setting member, whereby a push button is elevated from one end of the device, and the set dose can then be injected by pressing the push button back to its non-elevated position, thereby moving a lead screw co-operating with the piston in a cartridge and expelling a medicament out of the cartridge through a needle.

DESCRIPTION OF THE RELATED ART

From EP 0 327 910 is known an injection device in which a dose is set by rotating a tubular injection button engaging a threaded lead screw, thereby causing the injection button to elevate from the end of the injection device. By pressing down the injection button until abutment with a fixed stop, the threaded lead screw is moved a distance corresponding to the movement of the injection button. The lead screw mates a piston in a cartridge and medicine is expelled from the cartridge. This kind of injection device transmits the injection force directly to the piston of the cartridge but provides no gearing, i.e. the linear movement of the injection button corresponds exactly to the linear movement of the lead screw.

By directly transmitted injection force a small dose of medicament causes a very little movement of the injection button, and it is therefore an advantage with a gearing ratio between the injection button and the lead screw to make it more clear to the user whether the injection is foregoing or not. Users having reduced finger strength could at the same time want a reduced injection force to carry out an injection.

EP 1 568 389 describes a pen with a gearing and which has a very little loss of energy due to friction and thereby a low injection force. A nut is rotated along a threaded lead screw. The nut is provided with a vertical gearwheel with an axis perpendicular to the axis of the nut, which on one side engages the housing and on the other side elevates an injection button. When the injection button is pushed, the nut and the lead screw are moved with a gearing ratio of 2:1 between the injection button and the lead screw. This mechanism provides a very few surfaces sliding against each other and the loss of force due to friction is therefore very limited. However, this mechanism is rather complicated and it is not suited for simple, disposable dose delivery devices.

WO 2005/018721 describes a pen with a gearing mechanism based on a first and a second thread handed in the same direction and a third thread on the lead screw which is not directly a part of the gearing mechanism. A lead screw is connected with a nut. A non-rotational driver is engaging a dial via a first thread and the dial is engaging the housing via a second thread. The pitch of the second thread is bigger then the pitch of the first thread and the difference between them is equal to the pitch of the lead screw. The driver is also axial connected with the nut. When the dose selector is rotated to set a dose, both the nut and the dial are rotated and the nut and the driver elevate a distance corresponding to the amount of drug to be injected while the dial elevates a longer distance. When the set dose is to be injected, the nut is rotational locked to the driver. As the dial is pushed into the device, the rotation of the dial will cause the non-rotational driver to retract into the dial and the resulting displacement of the driver to be equal to the set dose. The nut is now pushed back to the zero position bringing the lead screw along and causing insulin to be expelled.

In the device described in WO2009039851 the dose force is very low due to a gearing comprising a gearing nut with a first thread engaging the housing and a second thread engaging a driver both with very high pitches. The driver is rotationally locked to the housing. The two threads are handed in opposite directions. The gearing ratio is calculated as the ratio between the two pitches+1, ((pitch 1/pitch 2)+1). The gearing nut is axially connected to a dosing nut which is threadedly connected to a non-rotating lead screw. When a dose is set the dosing nut is rotated and elevated via a dose selector, but due to the gearing the dose selector is elevated even further by means of the driver. The dose selector also acts as a push-button. When the push-button is pushed and the set dose is injected, the driver is pushed down and the gearing nut is thereby rotated between the driver and the housing. This causes it to move axially but a smaller distance than the driver. During injection the dosing nut is prevented from rotating and the gearing nut now pushes the dosing nut and the lead screw which causes medicine to be expelled. A dial is coupled to the dose selector when a dose is set. When the dose is injected, the dial is decoupled, and the dial is pushed down by the driver which will cause it to rotate due to a thread engagement with the housing.

The above invention provides a convenient device with a very low dose force, but it is rather complicated to produce and the diameter for the sliding surfaces between the driver and the dial is rather big, which makes it sensible to friction.

It is an objective of the invention to provide a dose delivery device with a gearing which has a very low injection force, which is not sensible to friction and which is suitable for automated assembling.

BRIEF DESCRIPTION OF THE INVENTION

The objectives of the invention can be obtained by a dose delivery device comprising a housing, a dose setting system further comprising a dial and a dose setting member and a dose injecting system further comprising a push-button a lead screw rotationally locked to the housing and a gearing mechanism. The gearing mechanism further comprises a first gearing member, a driver connected to the first gearing member in a track allowing axial movement, and a second gearing member being provided between the driver and the first gearing member (this will be further explained later).

The dose setting system is of a kind, where a dial is engaged with the housing via a thread and rotationally coupled to a dose setting member when a dose is set, and rotationally decoupled when a set dose is injected. The dial, the driver and the dose setting member moves up the same distance when a dose is set. A dose is set by rotating the dose setting member which carries the dial along. During injection the dial is decoupled from the dose setting member and pushed down which causes it to rotate due to the thread engagement with the housing. The sliding surfaces on the dose setting member and the dial are in the top of the device and they can consequently have a very little diameter and thereby cause a very little loss of energy.

The rotational coupling between the dial and the dose setting member is a ratchet which can be either unidirectional or bidirectional. The torque between the parts due to resistance in the ratchet should be higher than the torque due to friction between the dial and the housing, as this will cause the dose setting member to carry the dial along. During injection the dose setting member does not rotate or it rotates less than the dial, and as the dial is forced to rotate in its thread engagement with the housing, it will cause the ratchet between the dose setting member and the dial to click.

In another embodiment the connection between the dial and the dose setting member is a more rigid connection comprising teeth on each part which can be engaged or disengaged.

The non-rotating lead screw cooperates with a piston in a cartridge. The lead screw is engaged with a dosing nut via a thread with a smaller pitch than the thread between the dial and the housing. The dosing nut is rotational locked to the gearing mechanism which will be further described below. To set a dose, the dose setting member and the gearing mechanism are rotated which will cause the dosing nut to elevate along the lead screw, but less than the elevation of the dial and the dose setting member. When a dose is injected, the force applied to the push-button is transferred to the dosing nut via the gearing mechanism which does not rotate during injection. As the dosing nut is rotational locked to the gearing mechanism and consequently does not rotate during injection and as also the lead screw is locked against rotation, the lead screw will be moved forward by the dosing nut, and the piston in the cartridge will expel medicine.

The gearing mechanism comprises a first (outer) and a second (inner) gearing member, and the dosing nut is rotationally connected to the first gearing member and axially connected to the second gearing member. The second gearing member comprises two threads which are headed in opposite directions, i.e. one is a normal right-handed thread and the other is a left-handed thread. The right-handed thread (or the left-handed thread) is connected with the first gearing member, and the other thread is connected with the driver which is rotationally locked to the dose setting member. The driver and the first gearing member are rotationally locked to each other. When a dose is set, the dosing nut will force the second gearing member to elevate along with the dosing nut and this will cause the second gearing member to rotate relative to the first gearing member due to the thread engagement between them. This will cause the driver (and thereby the dose setting member and the push-button) to elevate even further, as it is affected both directly by the elevation of the second gearing member and also by the relative rotation between the second gearing member and the driver, which also causes the driver to elevate as the thread is handed opposite to the thread between the second gearing member and the first gearing member.

So, when the first gearing member and the driver are moved longitudinally relative to each other, the second gearing member will rotate and move longitudinally as well but a distance smaller than the distance moved by the push-button. When the set dose is injected, the applied force on the push-button is transferred via the driver to the second gearing member and further on to the dosing nut and the lead screw. The pitches on the second gearing member can be set to any value as long as the threads are not self-locking as it is only the ratio between the pitches that defines the gearing ratio. This means that the loss of force on the piston due to friction can be very low.

When a dose is set, a clicking sound is produced. When the first gearing member is rotated ratchet arms in the first gearing member will move radial in and out in grooves in the housing, To prevent that a dose is set which is higher than the remaining content in the cartridge, the lead screw is not threaded in the one end and the dosing nut and thereby the driver and the dose setting member will therefore be blocked against further rotation when the end of the thread on the lead screw is reached.

It should be noted, that the dose delivery device can be designed to be either disposable or rechargeable and to contain one, two or multiple cartridges at the time. If the dose delivery device is designed to be rechargeable, the lead screw must be able to move back into the device when the cartridge holder is disconnected.

In another embodiment the first gearing member and the driver are rotationally connected via a helical track with a higher pitch than the threads on the second gearing member. This can make the relative rotation between the dial and the driver less, as the driver will rotate slightly during injection, and thereby the loss of energy will be less when the driver pushes down the dial during injection. If a very big gearing is desired, this also has the advantage that if the helical track and the thread pitch between the driver and the second gearing element are headed in the same direction, it can be avoided that the thread pitch becomes so high that the axial position of the second gearing element becomes inaccurate.

The dosing nut can either be rotationally connected to the first gearing member or to the driver.

In an even further embodiment the dosing nut is not present and the second gearing member with the two opposite handed threads are also engaging the lead screw via a third thread. This is possible as the second gearing member rotates together with the entire gearing mechanism as well as relative to the first gearing member when a dose is set, but only rotates relative to the first gearing member, when the dose is injected. Thereby the second gearing member does not rotate the same number of revolutions relative to the housing when a dose is set and when a dose is injected. The thread engagement between the second gearing member and the lead screw should have a pitch of a size that ensures, that the lead screw do not move axially when a dose is set. The non rotational connection between the lead screw and the housing can be replaced with a thread with the same pitch as between the first and the second gearing member to ensure that the lead screw and the second gearing member rotates together during injection. In this way it is ensured, that a dose higher than the remaining fluid in the cartridge, can not be set.

FIGURES

In the following the invention is described in further details with reference to the drawings, wherein.

DETAILED DESCRIPTION

In the following the term up refers to the direction towards the dose setting member 102 and the term down refers to the direction towards the needle end.

Figure 1:
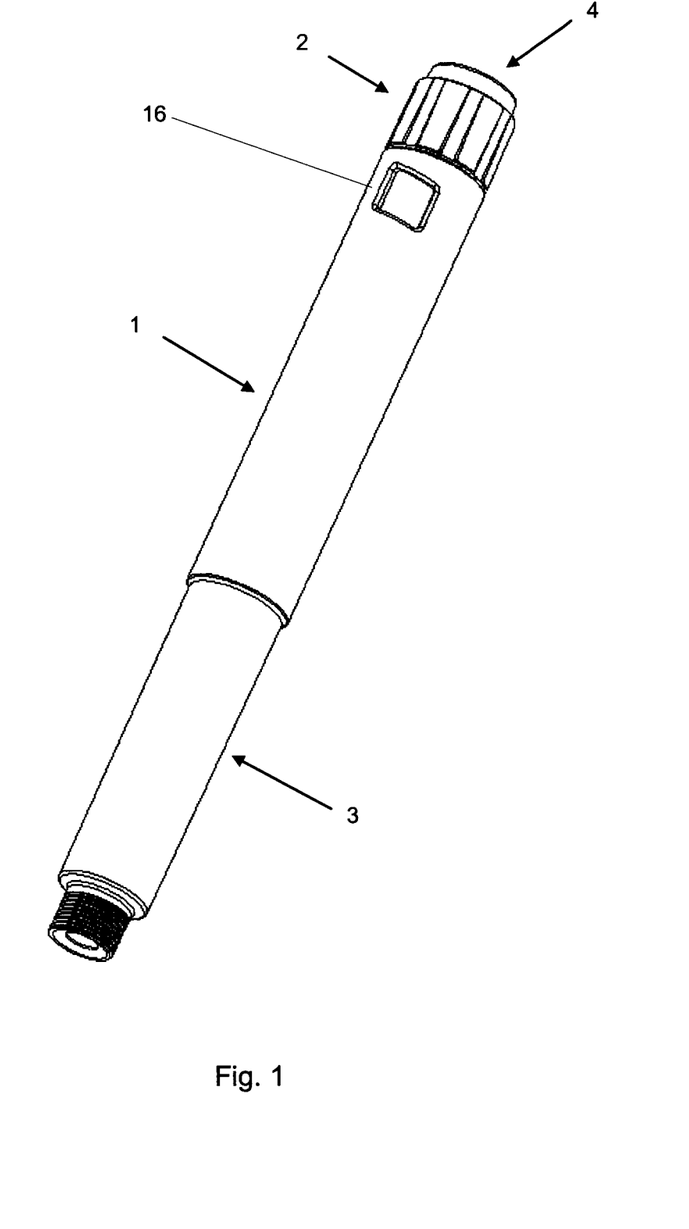
FIG. 1 shows a perspective view of an embodiment of a device according to the invention with a ratchet connection between the dial and the dose setting element.

FIG. 1 shows a device according to the invention in an oblique view. Visible is the housing 1 comprising a window 16, where the amount of a set dose can be displayed, the dose setting member 2 by which a dose is set, the push-button 4 by which a set dose is injected and the cartridge holder 3 comprising a thread for the attachment of a double-ended needle. The cartridge holder 3 contains the medicine-filled cartridge 12 (see FIG. 2). The cartridge 12 comprises a piston (see FIG. 3), which cooperates with the lead screw 10 of the injection system to expel a set dose of medicine from the cartridge 12 out through the needle. The cooperation between the different elements of the device will be described in the following.

Figure 2:
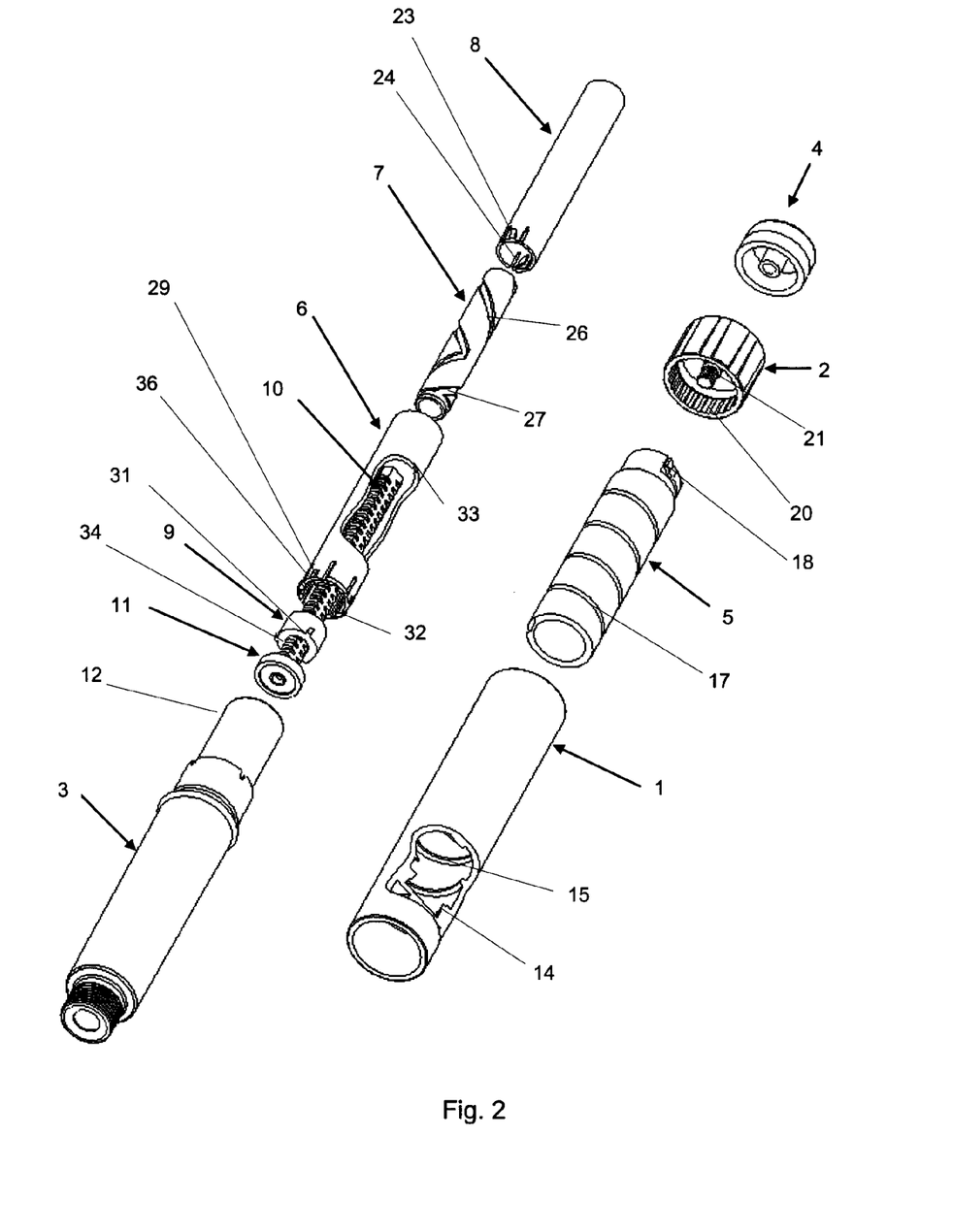
FIG. 2 shows an exploded view of an embodiment of a device according to the invention with a ratchet connection between the dial and the dose setting element, FIG. 3 schematically shows a vertical sectional view of an embodiment of a device according to the invention with a ratchet connection between the dial and the dose setting element and ready to set a dose, FIG. 4 schematically shows a vertical sectional view of an embodiment of a device according to the invention with a ratchet connection between the dial and the dose setting element and where a dose has been set, FIG. 5 schematically shows a vertical sectional view of an embodiment of a device according to the invention with a ratchet connection between the dial and the dose setting element and where the set dose has been injected.
Figure 3:
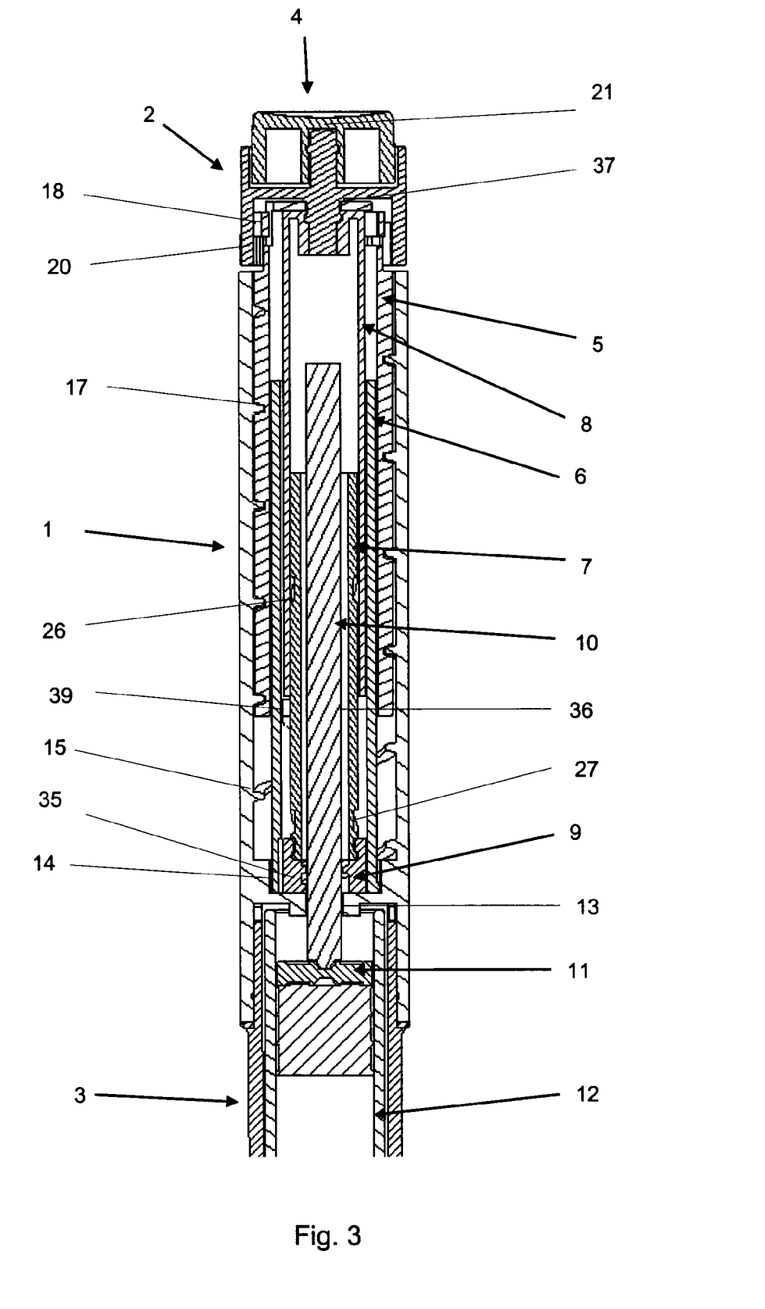

As shown in FIG. 3, a dosing nut 9 is engaged with a lead screw 10 via a thread connection 34/35 (the thread 34 on the lead screw visible on FIG. 2). The lead screw 10 is locked against rotation relative to the housing 1 via a key/groove connection 13/36. The dosing nut 9 is rotational locked to a first gearing member 6 (key/groove connection 31/32, see FIG. 2) which is rotational locked to a driver 8 and a dose setting member 2, the driver 8 being fixed in the dose setting member 2 so that they act as one part. The first gearing member 6 has a number of protrusions 29 (see FIG. 2) in the bottom which cooperates with grooves 14 in the housing 1 so that when the dose setting member 2 is rotated, the first gearing member 6 will be indexed at certain positions equally spaced around the revolution, and at the same time a clicking sound is made when a dose is set.

A gearing mechanism is comprising the first gearing member 6, a second gearing member 7 and the driver 8 and is situated between the dosing nut 9 and the dose setting member 2 in such a way, that when the dose setting member 2 is being rotated to set a dose, the dosing nut 9 will rotate as well and this will elevate the dosing nut 9 due to the thread engagement 34/35 with the lead screw 10, but the driver 8 and the dose setting member 2 will be elevated a bigger distance due to the gearing mechanism. The gearing mechanism is provided to make it easier to inject a set dose, to make it more visible to the user that the push-button is being moved during injection and to provide more space for numbers to be written on a dial 5.

The second gearing member 7 is axially connected to the dosing nut 9 but is capable of rotating relative to the dosing nut 9. This can be seen in FIG. 3. There are two threads on the outer surface of the second gearing member 7, which are headed in opposite directions, i.e. one is a normal right-handed thread and the other is a left-handed thread. The right-handed thread is engaged with the first gearing member 6 and the left handed thread is engaged with the driver 8. When a dose is set, the dosing nut 9 will force the second gearing member 7 to elevate along with the dosing nut 9 due to the axial connection and this will cause the second dose member 7 to rotate due to the thread engagement 27/39 with the first gearing member (see FIG. 3). This will cause the driver 8 to elevate more than the second gearing member 7 as it is affected in two ways: It is axially elevated by the second gearing member 7 and it is rotated in the thread engagement 24/26 between the two elements. Because the thread is handed opposite to the thread connection 26/39 between the second gearing member 7 and the first gearing member 6 this will cause the driver 8 to elevate further.

This means that when the first gearing member 6 and the driver 8, which are relative rotationally locked via the key/groove 23/33, are moved axially relative to each other, the second gearing member 7 will rotate and move axially a distance smaller than the axially distance moved by the driver 8. When a dose is injected the applied force on the push-button 4 is transferred to the dosing nut 9 via the dose setting member 4, the driver 8 and the second gearing member 7. A gearing in distance is achieved as the driver 8 moves a longer distance than the dosing nut 9 and the lead screw 10, and a gearing in force is achieved, as the loss of force due to friction is lower than the extra force due to the gearing.

The pitches of the threads on the second gearing member 7 can be set to any value as long as the threads are not self-locking and they can thereby be set to be very high. This is very advantageous as it means that the loss of dosing force due to friction can be very low.

The directions of the two threads on the double nut can be interchanged, so that the right-handed thread is left-handed and vice versa. The important matter is that they are headed in opposite directions.

To be able to display the amount of a set dose, a numbered dial 5 is part of the device. This can most clearly be seen on FIG. 3. The dial 5 engages with the housing 1 via a thread connection 15/17. The dial 5 has two ratchet arms 18 which interact with teeth 20 on the inner cylindrical surface of the dose setting member 2. When the dose setting member 2 is rotated to set a dose, the ratchet arms 18 will rotate the dial 5 along as the resistance between the dose setting member 2 and the dial 5 due to the ratchet arms 18 is higher than the resistance in the thread between the dial 5 and the housing 1 due to friction. When a set dose is corrected the dose setting member 2 is rotated in the locking direction of the one ratchet arms 18, and the dial 5 will rotate along.

To reduce the loss of energy between the dial 5 and the dose setting member 2 further when a dose is injected, the connection 23/33 between the driver 8 and the first gearing member 6 can be formed as a helical track with a higher pitch than the pitches of the second gearing member 7. This will cause the dose setting member 2 to rotate slowly when a set dose is injected and if the rotational direction is arranged to be the same direction as for the dial 5, the relative movement between the dial 5 and the dose setting member 2 will be smaller and the loss of energy will be reduced correspondingly. The pitch of the thread 26 on the second gearing member 7 and the number of increments between the housing 1 and the first gearing member 6 has to be corrected accordingly to make this embodiment work. Other corrections of parts will also be needed.

FIG. 3 shows a device ready for setting a dose. To set a dose, the dose setting member 2 is rotated, which will cause the device to produce a clicking sound for each increment due to the click protrusions 29 on the first gearing member 6 which cooperates with the grooves 14 in the housing 1, each click corresponding e.g. to a unit of the medicine in the cartridge. Furthermore, this interface will provide a number of preferred positions of the dose setting member. The dose setting member 2 rotates the driver 8 and the first gearing member 6, and this will now elevate the dosing nut 9 (rotational locked to the first gearing element 6 via key groove connection 31/32) from a zero position. The driver 8 will elevate as well, but because of the gearing mechanism, it will elevate more than the dosing nut 9. The dial 5 is rotated along with the dose setting member 2 due to the engagement with the ratchet arms 18 on the dial 5 and it elevates a distance corresponding to the elevation of the driver 8.

Figure 4:
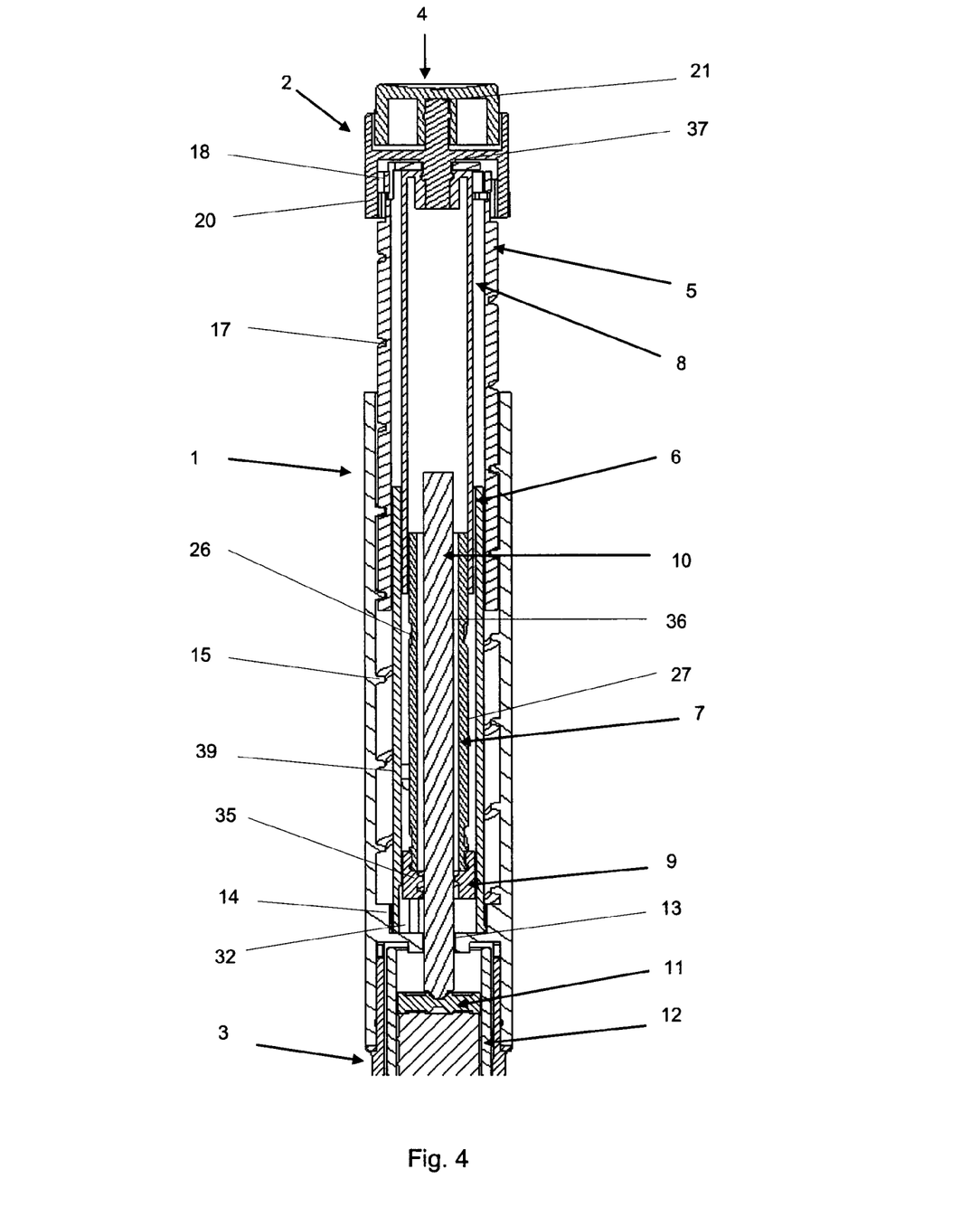

In FIG. 4 a dose has been set and the device is ready to inject. The dose setting member 2, the driver 8 and the first gearing member 6 has been rotated and it can clearly be seen, that the dial 5, the driver 8, the dose setting member 2 and the push-button 4 has moved one distance, and that the second gearing member 7 and the dosing nut 9 has moved another and smaller distance.

Figure 5:
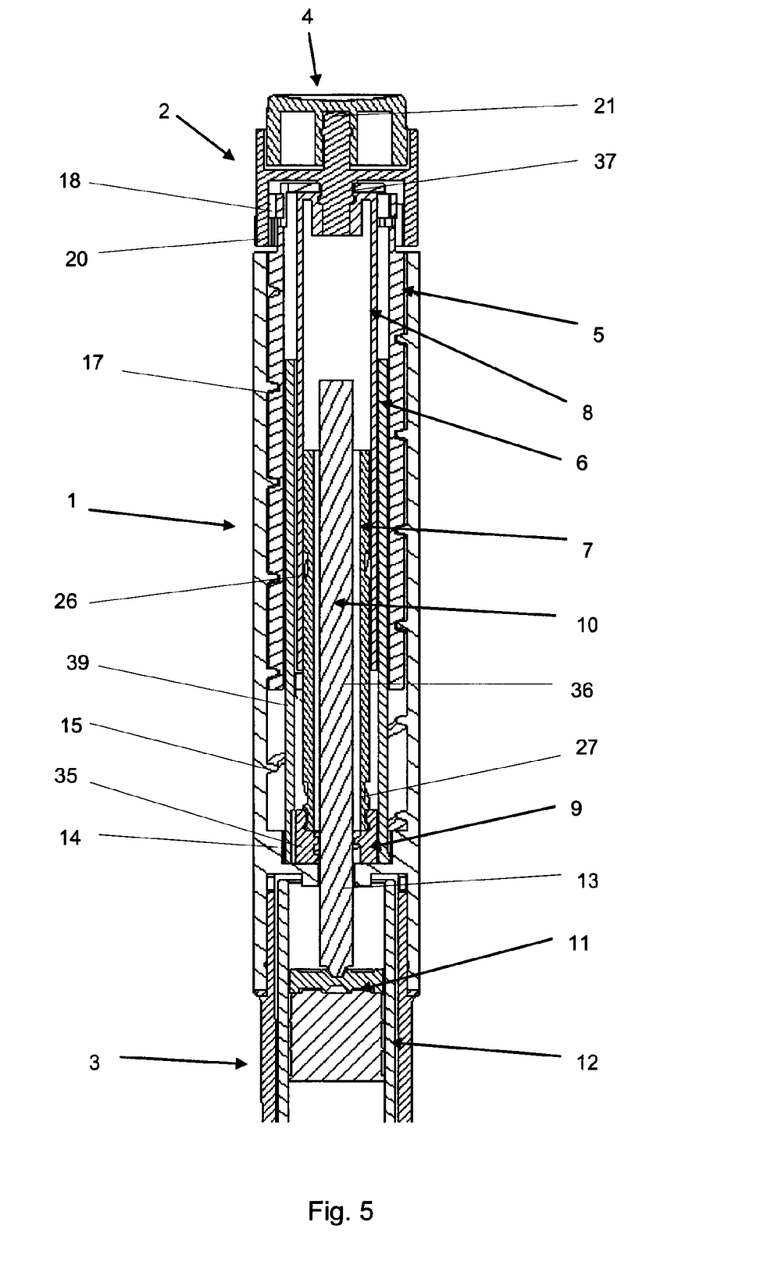

In FIG. 5 the set dose has been injected. The push-button 4 has been pushed which has pushed down the driver 8 and rotated and moved down the second gearing member 7. However, the second gearing member 7, the dosing nut 9 and the lead screw 10 has moved down a smaller distance than the push-button 4, the driver 8 and the dose setting member 2. The dial 5 has been pushed down and rotated back to the zero position and a clicking sound has been produced due to the interaction between the teeth 20 inside the dose selector 2 and the ratchet arms 18 on the dial 5. The pushing force is provided via a sliding surface 37 on the dose setting member 2. As this connection is in the push-button end of the device and above the driver, it can be situated on a very little diameter with a very little loss of energy as a consequence. This is very advantageous. It can be seen that the lead screw 10 has moved a distance corresponding to the movement of the dosing nut 9 when the dose was set. Consequently also the piston washer 11 and the piston in the cartridge have moved and the medicine has been expelled.

Figure 6:
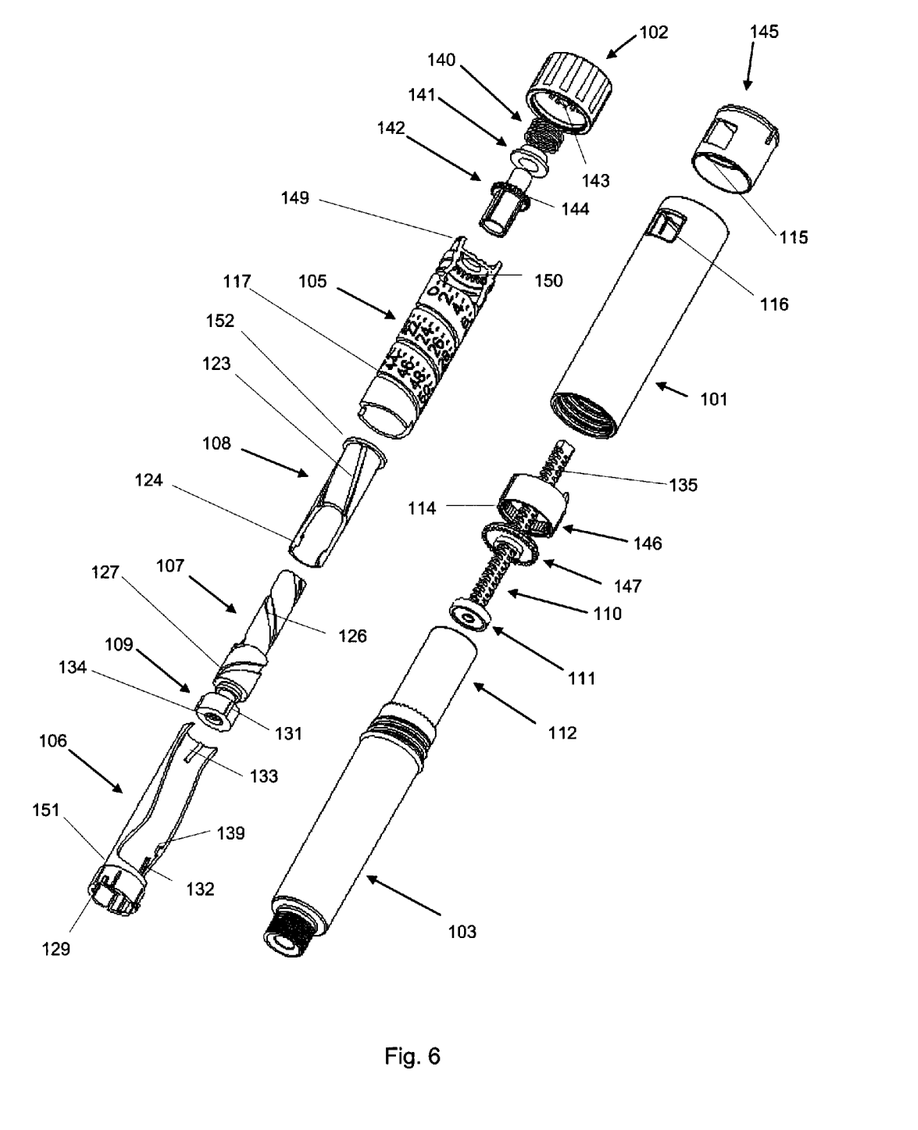
FIG. 6 shows an exploded view of an embodiment of a device according to the invention with a teeth connection between the dial and the dose setting element, FIG. 7 schematically shows a vertical sectional view of an embodiment of a device according to the invention with a teeth connection between the dial and the dose setting element and ready to set a dose.
Figure 7:
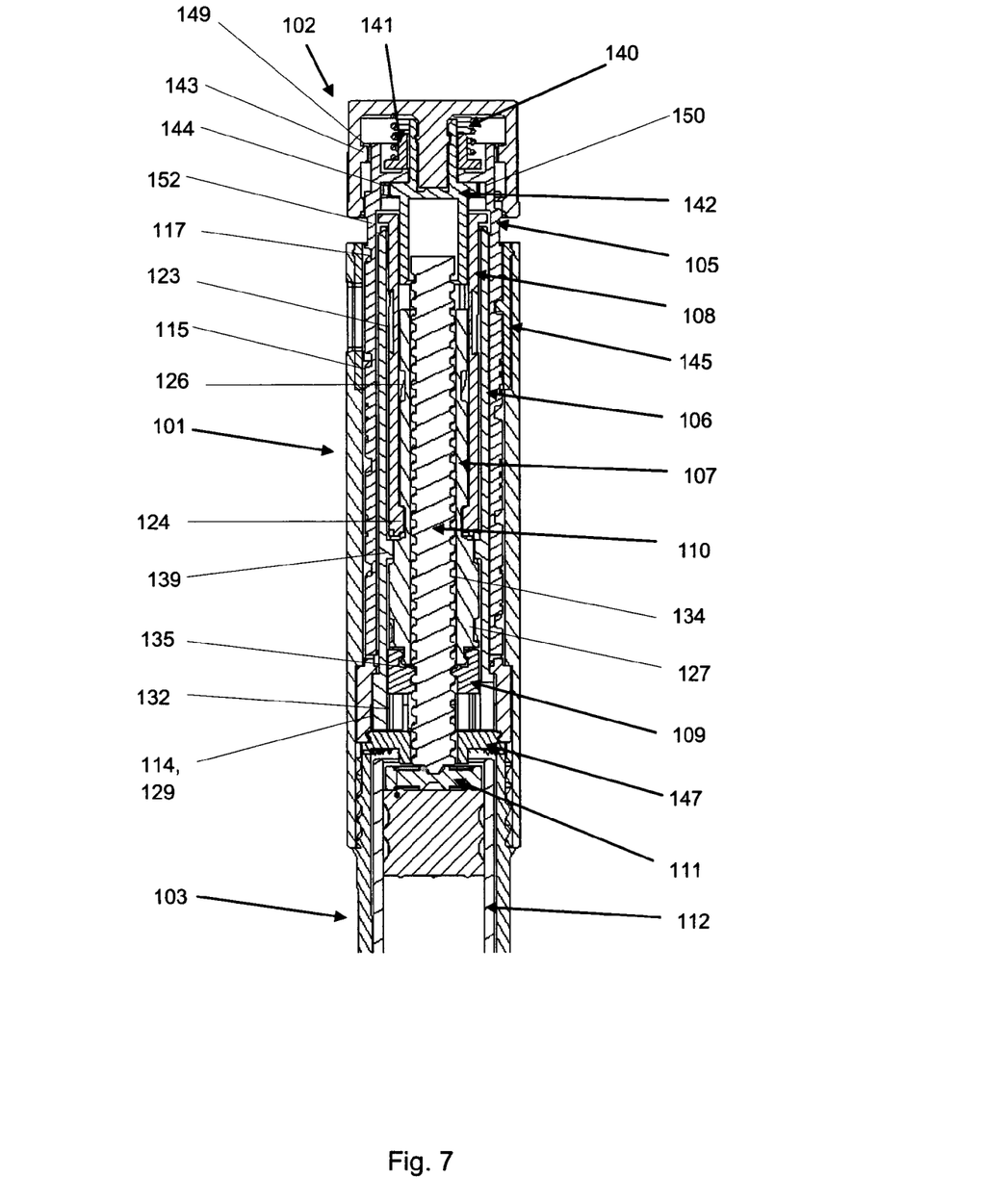

FIGS. 6 and 7 shows another embodiment according to the invention with a helical track between the first gearing member 106 and the driver 108, with a releasable teeth connection between the dial 105 and the dose setting member 102 and with the dose setting member 102 also acting as push-button. As can be seen on FIG. 7 the dosing nut 109 is engaging the lead screw 110 via a thread connection 134/135 and is axial but not rotational connected with the second gearing member 107 and rotational but not axial connected with the first gearing member 106 via the teeth 131 on the dosing nut 109 and grooves 132 inside the first gearing member 106. The lead screw 110 is locked against rotation relative to the housing by a locking part 147 fixed in the housing 101 in which the lead screw 110 can slide down without rotating. The thread 127 on the second gearing member 107 is engaging the thread segments 139 on the first gearing member 106 and the thread 126 on the second gearing member 107 is engaging the thread segments 124 on the driver 108. The first gearing member 106 and the driver 108 are further more connected via a helical track 123 on the driver 108 and track segments 133 on the first gearing member 106 (the respective threads and tracks can best be seen on FIG. 6). The first gearing member 106 is capable of rotating relative to the housing 101 producing a clicking sound by means of a click protrusion 129 cooperating with teeth 114 in a click bushing 146 fixed in the housing 101 (best seen on FIG. 6). A connector 142 is axial connected to the dose setting member 102 and rotational connected to the driver 108 via keys on the connector 142. The dose setting member 102 and the connector 142 are snapped together and are allowed to move axially a short distance by which movement the teeth 143 on the dose setting member 102 is disengaging the teeth 149 on the numbered dial 105 and the teeth 144 on the connector 142 is disengaging the teeth 150 on the numbered dial 105. A spring 140, a spring bushing 141 and the dose setting member 102 is connected with the dial 105 and the connector 142 in such a way, that the spring 140 and the spring bushing 141 will try to push the dial 105 back into engagement with the dose setting member 102 and the connector 142. A flange 152 on the driver 108 snaps into the dial 105 such that only rotational movement between the two parts are allowed and such that the dial 105 cannot be pushed to far relative to the injection. The dial 105 is via a thread connection 115/117 engaging a threaded element 145 which is fixed in the housing 101.

When the dose setting member 102 is rotated to set a dose the dial 105 will be rotated as well due to the teeth engagement 143/149 between the parts. The teeth engagement 144/150 between the dial 105 and the connector 142 ensures that the connector 142 will be rotated as well and thereby also the driver 108 and the first gearing member 106, however, the first gearing member 106 will rotate less than the driver 108 due to the helical path connection 123/133 between the two parts and the relative axial movement between them. The first gearing member 106 will produce a clicking sound during dose setting and index the dose setting at specific positions corresponding to specific amounts of drug due to the protrusion 129 on the first gearing member 106 cooperating with the teeth 114 inside the click bushing 146. The dosing nut 109 and the second gearing member 107 will be pushed up due to the thread engagement between the dosing nut 109 and the lead screw 110 and this will rotate the second gearing member 107 due to the thread engagement 127/133 with the first gearing member 106. The driver 108 will now be both pushed up and rotated up by the second gearing member 107 due to the thread connection 124/126 between them and consequently it will move up higher than the dosing nut 109 and the second gearing member 107. The dial 105 will move up the same distance as the driver 108 due the thread connection 115/117 with the threaded element 145 fixed in the housing 101.

When the dose setting member 102 is pushed and the set dose is injected, the dose setting member 102 and the connector 142 is disengaged from the dial 105. After the connector 142 has reached the end of the key/groove connection with the driver 108, the driver 108 will be pushed down. The first gearing member 106 does not rotate during injection and the driver 108 and the connector 142 will rotate slightly. The second gearing member 107 will be pushed down by the driver 108 but due to the two opposite handed threads 126/127 on the second gearing member 107 which are engaging the thread segment 133 on the first gearing member 106 and the thread segment 124 on the driver 108 it will move a smaller distance. The first gearing member 106 and the dosing nut 109 does not rotate during injection so when the dosing nut 109 is pushed down it will also push down the non-rotating lead screw 110 and this will push down the foot 111 and the piston in the cartridge 112 and medicine will be expelled through the needle.

The invention claimed is:
1. A dose delivery device comprising:
   a gearing mechanism including
      a first gearing member with a first thread,
      a driver with a second thread,
      a second gearing member with two threads engaging the first and the second thread respectively,
   a housing for interfacing a user and wherein the gearing mechanism is coaxially arranged,
   a dose setting member rotationally connected to the gearing mechanism during dose setting,
   a lead screw,
   a dosing nut engaged with the lead screw via a thread, the dosing nut axially connected to the second gearing member, the dosing nut rotationally connected to the first gearing member,
   wherein the first and the second threads are headed in opposite directions and
   wherein the first gearing member and the driver are rotational connected via a track allowing axial movement, and
   wherein the gearing mechanism rotates relative to the housing when a dose is set by rotating the dose setting member.

2. A device according to claim 1 wherein the track between the first gearing member and the driver does not allow rotational movement between the parts.

3. A device according to claim 1 wherein the rotational connection between the first gearing member and the driver is a helical track.

4. A device according to claim 1 wherein a dial which is threadedly engaged with the housing is rotated together with the dose setting member when a dose is set, and not rotated together with the dose setting member, when the dose is injected.

5. A device according to claim 4 wherein the dial is connected to the dose setting member via a one-way ratchet.

6. A device according to claim 4 wherein the dial is connected to the first gearing member via a one-way ratchet.

7. A device according to claim 1 wherein the lead screw is rotationally locked to the housing.

8. A device according to claim 1 wherein the dose setting member is rotationally connected to the driver during dose setting.

* * * * *